United States Patent [19]

Fanshawe et al.

[11] Patent Number: 5,001,157

[45] Date of Patent: Mar. 19, 1991

[54] SUBSTITUTED N-[[2-(AMINOCARBONYL)-PHENYLAMINO]THIOXOMETHYL]BENZAMIDES

[75] Inventors: William J. Fanshawe, Pearl River; Joseph W. Epstein, Monroe, both of N.Y.

[73] Assignee: American Cyanamid Company, Wayne, N.J.

[21] Appl. No.: 305,031

[22] Filed: Feb. 2, 1989

[51] Int. Cl.$^5$ .................... A01N 47/28; A61K 31/17
[52] U.S. Cl. ........................................ 514/584; 564/23
[58] Field of Search .................. 564/23; 514/584, 596

[56] References Cited

U.S. PATENT DOCUMENTS

| | | | |
|---|---|---|---|
| 3,985,898 | 10/1976 | Jackson | 514/584 |
| 4,101,675 | 7/1978 | Panneman | 564/23 |
| 4,550,202 | 10/1985 | Brouwer et al. | 564/23 |
| 4,623,662 | 11/1986 | DeVries | 514/596 |

FOREIGN PATENT DOCUMENTS

| | | |
|---|---|---|
| 017484 | 10/1980 | European Pat. Off. |
| 0241738A | 12/1986 | German Democratic Rep. ........... 514/584 |

OTHER PUBLICATIONS

Sirrenberg et al., *Chemical Abstracts*, vol. 105, 172068f (1986).

Chan et al., *Heterocycles*, vol. 26, No. 12, 1987, pp. 3193 to 3196.

*Primary Examiner*—Glennon H. Hollrah
*Assistant Examiner*—Scott C. Rand
*Attorney, Agent, or Firm*—Kenneth J. Dow

[57] ABSTRACT

New substituted N-[[2-(aminocarbonyl)phenylamino]-thioxomethyl]benzamides which are useful as congnition stimulators in mammals.

14 Claims, No Drawings

SUBSTITUTED N-[[2-(AMINOCARBONYL)-PHENYLAMINO]THIOXOMETHY]BENZAMIDES

This disclosure describes novel substituted N-[[2-(aminocarbonyl)phenylamino]thioxomethyl]benzamides which are useful as cognition stimulators in mammals.

BRIEF SUMMARY OF THE INVENTION

This invention relates to new organic compounds and, more particularly, is concerned with novel substituted N-[[2-(aminocarbonyl)phenylamino]thioxomethyl]benzamides which may be represented by the following structural formula:

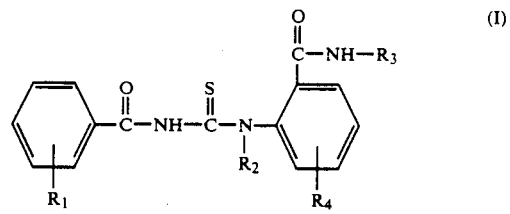

wherein $R_1$ is hydrogen, halogen, alkyl having from 1 to 3 carbon atoms or alkoxy having from 1 to 3 carbon atoms; $R_2$ is hydrogen or alkyl having from 1 to 3 carbon atoms; $R_3$ is hydrogen, phenyl or alkyl having from 1 to 3 carbon atoms; and $R_4$ is hydrogen, alkyl having from 1 to 3 carbon atoms or alkoxy having from 1 to 3 carbon atoms. These compounds are useful as cognition stimulators in mammals and have further utility as intermediates in the preparation of benzoylaminoquinazolinones which are also cognition stimulators.

DETAILED DESCRIPTION OF THE INVENTION

The compounds of the present invention may be prepared as set forth in the following reaction scheme.

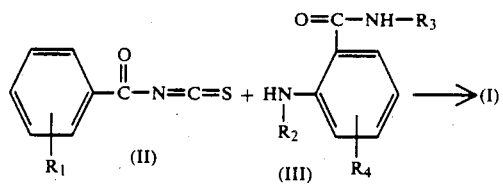

wherein $R_1$, $R_2$, $R_3$ and $R_4$ are as hereinbefore defined. In accordance with the above reaction scheme, a benzoyl isothiocyanate (II) is reacted with a 2-aminobenzamide (III) in an inert organic solvent such as diethyl ether, dimethylformamide or dioxane for several hours at ambient temperatures to provide the products (I) of the invention.

The novel compounds of the present invention possess the ability to enhance neural function in warmblooded animals affected by behavioral neurological problems, including the cognitive deterioration associated with decreased neural function which occurs with cerebral insufficiency, aging, dementia and similar conditions.

A useful in vivo test that measures hoW effectively central nervous system-acting drugs enhance survival in a hypoxic environment, by improving the ratio of energy supply to demand is known as the Hypoxic Survival Test. This test demonstrates the ability of the test compounds relative to a known parasympathomimetic agent physostigmine. This test shows the enhanced survival of test animals in a hypoxic environment after treatment with drug as compared to saline treated control animals without drug. Extensive testing has demonstrated that under conditions of 10% oxygen, only 5-2% of control mice (treated with saline) survive after 5 minutes, whereas 60-80% of the physostigmine treated mice survive. Drugs are tested by intraperitoneally injecting groups of mice 30minutes prior to placing them in a hypoxic mixture and measuring survival The rationale of this test is that drugs which enhance survival under hypoxic conditions Without concomitant, depression or sedative side effects, do so by enhancing energy metabolism, or by preserving normal brain function under conditions of reduced energy metabolism. Given the dependence of the brain on constant supply of energy, drugs which have this property have many far-reaching therapeutic indications, including recovery from stroke and closed head injury, as well as reducing the deleterious effects of the aging central nervous system. For example, in aged and senile demented patients, energy metabolism is known to be deficient, and is thought to contribute significantly to the neurochemical and neurophysiological dysfunctions of aging.

Groups of 20 Royal Hart mice (6 weeks of age) are injected intraperitoneally with test compound (1–200 mg/kg) 30 minutes prior to placing them in a hypoxic mixture (10% oxygen in 90% carbon dioxide) and measuring survival after 5 minutes A separate group of 20 mice is injected intraperitoneally with saline solution (0.01 ml/g of body weight) and processed as described above. Still another group of 20 mice is injected intraperitoneally with 0.125 mg/kg of physostigmine and processed as described above.

Results of this test on representative compounds of the present invention appear in Table I below.

TABLE I

| | Hypoxic Survival Test | |
|---|---|---|
| Compound | Dose (mg/kg) | % Survivors |
| N-[[[2-(Amiocarbonyl)phenyl]- methylamino]thioxomethyl]- benzamide | 50 100 200 | 55 50 45 |
| N-[[[(Aminocarbonyl)phenyl]- amino]thioxomethyl]benzamide | 100 200 | 52.5 50 |
| N-[[[2-(Amiocarbonyl)phenyl]- amino]tioxomethyl]-4-methyl- benzamide | 50 100 200 | 82.5 86.7 75 |
| N-[[[2-(Aminocarbonyl)phenyl] methylamino]thioxomethyl]-4- methoxybenzamide | 10 100 | 25 62.5 |
| N-[[[2-(Aminocarbonyl)phenyl] amino]thioxomethyl]-4- chlorobenzamide | 25 50 100 | 65 65 75 |
| N-[[[2-(Aminocarbonyl)phenyl] methylamino]thioxomethyl]-3- methylbenzamide | 100 200 | 40 55 |
| N-methyl-2-[[[(4-methylbenzoyl) amino]thioxomethyl]amino]- benzamide | 10 50 100 | 45 70 70 |
| N-[[[2-Aminocarbonyl)phenyl]- amino]thioxomethyl]-3-methyl- benzamide | 10 50 100 | 55 67.5 80 |
| N-[[[2-(Aminocarbonyl)phenyl] amino]thioxomethyl]-4-methyl- benzamide | 50 100 200 | 82.5 86.7 75 |
| N-[[[2-(Aminocarbonyl)penyl] amino]thioxomethyl]-4-methoxy- benzamide | 10 50 100 200 | 40 60 82.5 75 |

TABLE I-continued

Hypoxic Survival Test

| Compound | Dose (mg/kg) | % Survivors |
| --- | --- | --- |
| 2-[[(Benzoylamino)thioxo-methyl]amino]-N-methylbenzamide | 50 | 50 |
|  | 100 | 65 |
| 2-[[(Benzoylamino)thioxomethyl]amino]-5-methylbenzamide | 10 | 52.5 |
|  | 50 | 50 |
| 2-[[(Benzoylamino)thioxomethyl]amino]-N-phenylbenzamide | 100 | 65 |
| 3-[[(Benzoylamino)thioxomethyl]amino]-2-naphthalenecarboxamide | 10 | 55 |
|  | 100 | 50 |

The novel compounds of the present invention have been found to be useful as agents for the treatment of cognitive and related neural behavioral problems in mammals when administered in amounts ranging from about 5 mg to about 200 mg/kg of body weight per day. A preferred dosage regimen for optimum results would be from about 10 mg to about 50 mg/kg of body weight per day and such dosage units are employed that a total of from about 700 mg to about 3.5 g of the active compound for a subject of about 70 kg of body weight are administered in a 24 hour period. This dosage regimen may be adjusted to provide the optimum therapeutic response. A decided practical advantage is that these compounds are active orally as well as parenterally.

The active compounds may be administered orally, for example, with an inert diluent or with an assimilable edible carrier or they may be enclosed in hard or soft shell gelatin capsules, or they may be compressed into tablets or they may be incorporated directly with the food of the diet. For oral therapeutic administration, these active compounds may be incorporated with excipients and used in the form of tablets, troches, capsules, elixirs, suspensions syrups, wafers and the like Such compositions and preparations should contain at least 0.1% of active compounds. The percentage of the compositions and preparations may, of course, be varied and may conveniently be between about 2% to about 6% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir m y contain the active compound, sucrose as a sweetening agent, methyl and propylparabens as preservatives, a dye and flavoring such as cherry or orange flavor. Of course, and material used in preparing any dosage unit form should be pharmaceutically pure and substantially non-toxic in the amounts used. In addition, these active compounds may be incorporated into sustained release preparations and formulations.

These active compounds may also be administered parenterally or intraperitoneally. Solutions or suspensions of these active compounds as a free base or pharmacologically acceptable salt can be prepared in water suitably mixed with a surfactant such as sodium lauryl sulfate or an emulsifier or stabilizer such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be described in greater detail in conjunction with the following specific examples.

EXAMPLE 1

N-[[[2-(Aminocarbonyl)phenyl]methylamino]thioxomethyl]benzamide

To a stirred mixture of 3.0 g. of 2-methylaminobenzamide in 150 ml of ether was added dropwise, a solution of 3.26 g of benzoyl isothiocyanate in 50 ml of ether over 15 minutes. The mixture was stirred overnight, then the solid was collected, giving 5.2 g of the desired product as cream-colored crystals, mp 147°–150° C.

EXAMPLE 2

N-[[[2-(Aminocarbonyl)phenyl]amino]thioxomethyl)-benzamide

To a stirred mixture of 13.6 g of 2-aminobenzamide and 200 ml of ether Was added dropwise, a solution of 16.3 g of benzoyl isothiocyanate in 100 ml of ether over 30 minutes. After standing 48 hours, the solid Was collected, giving 28.4 g of the desired product as grey crystals, mp 190°–192° C.

EXAMPLE 3

N-[[[2-(Aminocarbonyl)phenyl]methylamino]thioxomethyl]-4-methylbenzamide

To a stirred mixture of 4.5 g of 2-methylaminobenzamide in 200 ml of ether was added dropwise, a solution of 5.6 g of 4-methylbenzoyl isothiocyanate in 100 ml of ether over 20 minutes After stirring overnight, the solid was collected, giving 8.9 g of the desired product as white crystals, mp 145°–147° C.

EXAMPLE 4

N-[[[2-(Aminocarbonyl)phenyl]amino]thioxomethyl]-4-methylbenzamide

To a stirred mixture of 5.4 g of 2-aminobenzamide and 200 ml of ether was added dropwise, a solution of 7.5 g of 4-methylbenzoyl isothiocyanate in 100 ml of ether over 30 minutes. After 48 hours, the solid was collected, giving 12.2 g of the desired product as grey crystals, mp 208°–210° C. (dec.).

EXAMPLE 5

N-[[[2-(Aminocarbonyl)phenyl]amino]thioxomethyl]-4-methoxybenzamide

To a stirred mixture of 7.5 g of 2-aminobenzamide and 150 ml of ether was added dropwise, a mixture of 1.0 g of 4-methoxybenzoyl isothiocyanate in ether over 15 minutes. After stirring overnight, the solid was collected, giving 14.2 g of the desired product as grey crystals, mp 193°–196° C.

EXAMPLE 6

N-[[[2-(Aminocarbonyl)phenyl]methylamino]thioxomethyl]-4-methoxybenzamide

To a stirred mixture of 8.3 g of 2-methylaminobenzamide and 150 ml of ether was added dropwise, a mixture of 1.0 g of 4-methoxybenzoyl isothiocyanate in ether over 45 minutes. After stirring overnight, the solid was collected, giving 11.7 g of the desired product as cream colored crystals, mp 140°–143° C.

EXAMPLE 7

N-[[[2-(Aminocarbonyl)phenyl]amino]thioxomethyl]-4-chlorobenzamide

To a stirred mixture of 10.5 g of 4-chlorobenzoyl isothiocyanate in 100 ml of tetrahydrofuran was added a mixture of 6.8 g of 2-aminobenzamide in 200 ml of tetrahydrofuran. After stirring for 3 hours, the solid was collected, giving 14.3 g of the desired product as grey crystals, mp 204°–206° C. (dec.).

EXAMPLE 8

N-[[[2-(Aminocarbonyl)phenyl]amino]thioxomethyl]-3-methylbenzamide

To a stirred mixture of 7.2 g of 2-aminobenzamide and 200 ml of ether was added dropwise, a solution of 10 g of 3-methylbenzoyl isothiocyanate over 10 minutes. After 48 hours, the solid was collected, giving 14.8 g of the desired product as grey crystals, mp 194°–196° (dec.).

EXAMPLE 9

N-[[[2-(Aminocarbonyl)phenyl]methylamino]thioxomethyl]-3-methylbenzamide

To a stirred mixture of 7.95 g of 2-methylaminobenzamide and 200 ml of ether was added dropwise, a solution of 10 g of 3-methylbenzoyl isothiocyanate in ether over 10 minutes. After 48 hours, the solid was collected, giving 15.5 g of the desired product as cream-colored crystals, mp 144°–145° C. (dec.).

EXAMPLE 10

N-Methyl-2-[[[(4-methylbenzoyl)amino]thioxomethyl]amino]benzamide

To a stirred mixture of 8.0 g of 2-amino-N-methylbenzamide and 200 ml of ether was added dropwise, a solution of 10 g of 4-methylbenzoyl isothiocyanate in 100 ml of ether over 1 hour. After stirring several hours, the solid was collected, giving 17.1 g of the desired product as white crystals, mp 198°–200° C. (dec.).

EXAMPLE 11

2-[[(Benzoylamino)thioxomethyl]amino]-N-methylbenzamide

To a stirred mixture of 12 g of 2-amino-N-methylbenzamide and 200 ml of ether was added dropwise, a solution of 13.1 g of benzoyl isothiocyanate in 100 ml of ether over 30 minutes. The solid was collected, giving 22 g of the desired product as cream-colored crystals, mp 203°–205° C. (dec.).

EXAMPLE 12

2-[[(Benzoylamino)thioxomethyl)amino]-5-methylbenzamide

A mixture of 15 g of 2-amino-5-methylbenzoic acid, 16 g of 1,1-carbonyldiimidazole and 500 ml of tetrahydrofuran was stirred for 2 hours at room temperature and then saturated with anhydrous ammonia with ice bath cooling. After 24 hours, 50 ml of water was added and the mixture was concentrated under reduced pressure to a solid residue. This solid Was partially dissolved in 500 ml of dichloromethane and then washed with 200 ml of 0.1 N sodium hydroxide and 200 ml of water. The dichloromethane solution was dried and concentrated to a solid Which Was crystallized from ethyl acetate/hexane, giving 3.0 g of 2-amino-5-methylbenzamide as straw-colored crystals, mp 171°–174° C.

To a stirred mixture of 4.5 g of 2-amino-5-methylbenzamide and 200 ml of ether was added dropwise, a solution of 4.9 g benzoyl isothiocyanate in 100 ml of ether over 20 minutes. After stirring overnight, the solid was collected, giving 8.7 g of the desired product as white crystals, mp 198°–201° C. (dec.).

EXAMPLE 13

2-[[(Benzoylamino)thioxomethyl]amino]-4,5-dimethoxybenzamide

A mixture of 23.7 g of 2-amino-4,5-dimethoxybenzoic acid, 19.5 g of 1,1'-carbonyldiimidazole and 600 ml of tetrahydrofuran Was stirred for 2 hours at room temperature and then saturated with anhydrous ammonia with ice bath cooling. After 24 hours, the reaction mixture was diluted with 50 ml of water, heated at reflux for 2 hours and then concentrated under reduced pressure to about 50 ml. This liquid was mixed with 100 ml of 0.1N sodium hydroxide and then extracted with three 200 ml portions of dichloromethane. The extracts were combined, dried and evaporated. The residue was crystallized from acetonitrile, giving 5.5 g of 2-amino-4,5-dimethoxybenzamide as light grey crystals, mp 135°–138° C.

To a stirred mixture of 4 g of 2-amino-4,5-dimethoxybenzamide and 200 ml of ether was added dropwise, e solution of 3.3 g of benzoyl isothiocyanate in 100 ml of ether over 15 minutes. After 24 hours, the solid was collected, giving 7 g of the desired product as white crystals, mp 204°–207° C. (dec.).

EXAMPLE 14

N-[[[2-(Aminocarbonyl)-4-methylphenyl]amino]thioxomethyl]-4-methylbenzamide

To a stirred mixture of 3 g of 2-amino-5-methylbenzamide and 200 ml of ether was added dropwise, a solution of 3.7 g of 4-methylbenzoyl isothiocyanate in 100 ml of ether over 3 minutes. After 24 hours, the solid was collected, giving 6 g of the desired product as off-white crystals, mp 208°-209° C. (dec.).

EXAMPLE 15

N-[[[2-(Aminocarbonyl)phenyl]amino]thioxomethyl]-2-methylbenzamide

To a stirred mixture of 4.9 g of 2-aminobenzamide and 200 ml of ether was added dropwise, a solution of 6.67 g of 2-methylbenzoyl isothiocyanate in 100 ml of ether over 15 minutes After a few hours, the solid was collected, giving 10.8 g of the desired product as grey crystals, mp 181°-185° C. (dec.).

EXAMPLE 16

N-[[[2-(Aminocarbonyl)phenyl]methylamino]thioxomethyl]-2-methylbenzamide

To a stirred mixture of 5.4 g of 2-methylaminobenzamide and 200 ml of ether was added dropwise, a solution of 6.67 g of 2-methylbenzoyl isothiocyanate in 100 ml of ether over 15 minutes. After standing several hours, the solid was collected, giving 9.5 g of the desired product as grey crystals, mp 150°-154° C. (dec.).

EXAMPLE 17

2-Methyl-N-[[[2-(methylaminocarbonyl)phenyl]amino]-thioxomethyl]benzamide

To a stirred mixture of 5.4 g of 2-amino-N-methylbenzamide and 200 ml of ether was added dropwise, a solution of 6.67 g of 2-methylbenzoyl isothiocyanate in 100 ml of ether over 15 minutes. After several hours, the solid was collected, giving 11 g of the desired product as light grey crystals, mp 172°-175° C. (dec.).

EXAMPLE 18

2-[[(Benzylamino)thioxomethyl]amino]-N-phenylbenzamide

To a stirred mixture of 1.0 g of 2-amino-N-phenylbenzamide and 500 ml of ether was added dropwise, a solution of 7.7 g of benzoyl isothiocyanate in 100 ml of ether over 20 minutes. After standing several hours, the solid was collected, giving 17.3 g of the desired product as cream- colored crystals mp 197°-200° C. (dec.).

EXAMPLE 19

3-[[(Benzoylamino)thioxomethyl]amino]-2-naphthalenecarboxamide

A mixture of 24.8 g of 3-amino-2-naphthoic acid, 21 5 g of 1,1'-carbonyldiimidazole and 600 ml of tetrahydrofuran was stirred for 3 hours at room temperature and then saturated with anhydrous ammonia at ice bath temperature. This mixture was diluted with 50 ml of water, heated at reflux for 1 hour and then evaporated at reduced pressure. The residue was mixed with 200 ml of 0.1 N sodium hydroxide and 100 ml of water and the solid collected, giving 20.3 g of 3 -amino-2-nephthalenecarboxamide as light brown crystals, mp 225°-230° C. (dec.).

To a stirred mixture of 9.3 g of 3-amino-2-naphthalenecarboxamide and 300 ml of ether was added dropwise, a solution of 8.2 g of benzoyl isothiocyanate in 100 ml of ether over 10 minutes The resulting solid was collected and crystallized from 1400 ml of hot acetonitrile, giving 11.1 g of the desired product as straw-colored crystals, mp 220°-223° C.

We claim:

1. Compounds of the formula:

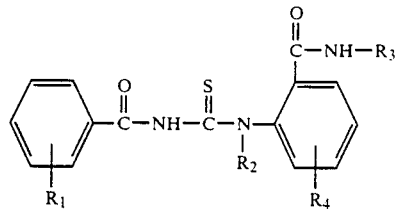

wherein $R_1$ is hydrogen, halogen, alkyl $(C_1-C_3)$ or alkoxy $(C_1-C_3)$; $R_2$ is hydrogen or alkyl $(C_1-C_3)$; $R_3$ is hydrogen, phenyl, or alkyl $(C_1-C_3)$ and $R_4$ is hydrogen, alkyl $(C_1-C_3)$ or alkoxy $(C_1-C_3)$ with the proviso that $R_1$, $R_2$, $R_3$ and $R_4$ may not all be hydrogen.

2. The compound according to claim 1; N-[[[2-(aminocarbonyl)phenyl]methylamino]thioxomethyl]-4-methylbenzamide.

3. The compound according to claim 1; N-[[[2-(aminocarbonyl)phenyl]amino]thioxomethyl]-4-methylbenzamide.

4. The compound according to claim 1; N-[[[2-(aminocarbonyl)phenyl]methylamino]thioxomethyl]-4-methoxybenzamide.

5. The compound according to claim 1; N-[[[2-(aminocarbonyl)phenyl]amino]thioxomethyl]-3-methylbenzamide.

6. The compound according to claim 1; N-[[[2-(aminocarbonyl)phenyl]amino]thioxomethyl]-4-methylbenzamide.

7. The compound according to claim 1; N-[[[2-(aminocarbonyl)phenyl]amino]thioxomethyl]-4-chlorobenzamide.

8. The compound according to claim 1; N-[[[2-(aminocarbonyl)phenyl]methylamino]thioxomethyl]-3-methylbenzamide.

9. The compound according to claim 1; 2-[[(benzoylamino)thioxomethyl]amino]-N-methylbenzamide.

10. The compound according to claim 1; N-methyl2[[[(4-methylbenzoyl)amino]thioxomethyl]amino]benzamide.

11. The compound according to claim 1; 2-[[(benzoylamino)thioxomethyl]amino]-5-methylbenzamide.

12. The compound 2-[[(benzoylamino)thioxomethyl]amino]-4,5-dimethoxy benzamide.

13. A method of treating cognitive and related neural behavioral problems in a mammal which comprises administering internally to said mammal a cognition stimulating amount of a compound of claim 1.

14. A cognition stimulating composition of matter in dosage unit form comprising from about 25 to about 500 mg of a compound of claim 1 in association with a pharmaceutically acceptable carrier.

* * * * *